(12) United States Patent
Forcales et al.

(10) Patent No.: US 8,629,983 B2
(45) Date of Patent: Jan. 14, 2014

(54) ASSEMBLY WITH ABSORBING SENSOR LAYER

(75) Inventors: Manuel Forcales, Barcelona (ES);
Jaime Gomez Rivas, Eindhoven (NL);
Marcus Verschuuren, Tilburg (NL);
Vincenzo Giannini, Viggiano (IT)

(73) Assignee: Stichting IMEC Nederland, Eindhoven (NL)

( * ) Notice: Subject to any disclaimer, the term of this patent is extended or adjusted under 35 U.S.C. 154(b) by 123 days.

(21) Appl. No.: 13/120,737

(22) PCT Filed: Sep. 24, 2009

(86) PCT No.: PCT/IB2009/054181
§ 371 (c)(1),
(2), (4) Date: May 26, 2011

(87) PCT Pub. No.: WO2010/035232
PCT Pub. Date: Apr. 1, 2010

(65) Prior Publication Data
US 2011/0222066 A1    Sep. 15, 2011

(30) Foreign Application Priority Data
Sep. 24, 2008   (EP) .................................... 08305585

(51) Int. Cl.
*G01N 21/55*    (2006.01)

(52) U.S. Cl.
USPC ........................................................ 356/445

(58) Field of Classification Search
None
See application file for complete search history.

(56) References Cited

U.S. PATENT DOCUMENTS 5,415,842 A  *  5/1995  Maule ........................ 422/82.05
5,980,831 A     11/1999  Braiman et al.

FOREIGN PATENT DOCUMENTS

EP       1780546       5/2007
WO    WO01/88509     11/2001

OTHER PUBLICATIONS

International Search Report, PCT International Application No. PCT/IB2009/054181 dated Dec. 2, 2009.
Written Opinion, PCT International Application No. PCT/IB2009/054181 dated Dec. 2, 2009.
Zhang, et al., "Surface wave sensors based on nanometric layers of strongly absorbing materials", Optics Express, vol. 20, No. 9, pp. 9431-9441, Apr. 23, 2012.

* cited by examiner

*Primary Examiner* — Kara E Geisel
*Assistant Examiner* — Amanda Merlino
(74) *Attorney, Agent, or Firm* — McDonnell Boehnen Hulbert & Berghoff LLP (57) ABSTRACT

The invention relates to an assembly for detecting the presence of a target based on a detection of a resonance associated to surface polaritons, such as long-range surface exciton polaritons (LRSEP). The invention relates to an assembly to be used in connection with a bio-sensor. The assembly comprising a carrier substrate (1) and a sensor layer (2) positioned on the carrier substrate. The sensor layer is of a material having a complex permittivity with an imaginary part being greater than or similar to the real part.

20 Claims, 4 Drawing Sheets

ASSEMBLY WITH ABSORBING SENSOR LAYER

FIELD OF THE INVENTION

The invention relates to an assembly for detecting the presence of a target, and in particular to an assembly where a target is detected based on a detection of a resonance associated to surface polaritons. Moreover, the invention relates to an optical detection system comprising an assembly, and to a method for detecting the presence of a target on an assembly.

BACKGROUND OF THE INVENTION

Detection methods for particular biological molecules (bio-molecules) are manifold and several different approaches are presently available to the skilled person. In one method low concentrations of a bio-molecule (the target) in a liquid analyte mixture are detected by means of detection of Surface Plasmon Resonances (SPR).

Surface plasmon resonance (SPR) based biosensors detect changes in a sample by detecting changes in the index of refraction of the sample, and thus do not require any fluorescent or other labelling of the sample. Accordingly, they are known as label-free biosensors. A change in the sample causes a change in the index of refraction of the sample, which is also reflected in a frequency change, a wavelength change or other measures, which typically is measured to determine the change in the index of refraction of the sample and thereby a change in the sample.

The principle of surface plasmon resonance biosensors can be extended to a general change in surface polariton resonances. A polariton is an electromagnetic wave coupled to a polarization excitation is solids. When this coupled excitation is bound to the interface between two media it is called a surface polariton (SP).

In SP-based sensors, one known technique consists in exciting a so-called long-range surface plasmon polariton (LRSPP). An LRSPP consists of coupled surface plasma waves existing on opposite sides of a thin conducting film suspended between two dielectrics. For a system where the long-range surface polariton is coupled between opposite faces of a non-conducting material is often referred to as a long-range surface exciton polariton (LRSEP). The advantage of LRSPP-based and LRSEP-based detection is a decreased resonance width and thereby an increased sensitivity, as compared to standard SPR-based detection. In LRSPP-based and LRSEP-based sensors, the electromagnetic field is less confined to the surface of the sensing layer. Therefore these types of sensors are interesting in connection with detection of large molecules, such as viruses.

The typical SP-based sensor, including the LRSPP-based sensor, is based on having a thin conducting metallic film as the sensor layer in which the excitation occurs. In the published international patent application WO 01/88509 it is disclosed to use a metallic or semiconducting material for supporting surface plasmon polaritons, however it is also specified in the specification of the application, that materials with a small value of refractive index n (real part of the complex permittivity) and a large k (imaginary part of the complex permittivity) that will generate a surface wave. Such a material is generally considered as a material having metallic properties.

The inventors of the present invention have appreciated that an improved way of performing surface polariton measurements is of benefit, and have in consequence devised the present invention.

SUMMARY OF THE INVENTION

In a typical SP-based biosensor, including the LRSPP-based sensor, the surface plasmon supporting material is a material which does not absorb electromagnetic radiation. More specifically, the material is a metal or a material possessing metallic properties. The inventors of the present invention have realized that by using a different type of sensor material, the general applicability of an SP-type biosensor may be expanded, for example, the applicable wavelength of the radiation is limited by the choice of the surface plasmon supporting material, by using a different type of material, a larger spectral region may become accessible.

It may be seen as an object of the present invention to provide an assembly suitable for SP-type detection with an improved sensitivity, and to provide an assembly which is applicable in a different or broader spectral region as is known in SP-type sensors of the prior art. In general, it may be seen as an object of the invention to provide a bio-sensor which is based on an alternative sensor material than the sensor materials known in the art.

In general, the present invention seeks to provide improved means for detecting a target, such as a biological target. Preferably, the invention alleviates, mitigates or eliminates one or more disadvantages of the prior art, singly or in any combination.

To this end, in a first aspect, the invention relates to an assembly for detecting the presence of a target, the assembly comprising a carrier substrate; and a sensor layer positioned on the carrier substrate;

wherein the sensor layer is of a material having a complex permittivity with an imaginary part being greater than or similar to the real part.

In a situation of use, the sensor layer may be covered by a medium, which in embodiments may be a liquid dielectric layer comprising the target, such as the liquid analyte mixture. Such a configuration supports excitation of long-range surface polaritons. By providing an assembly where the detection principle is based on coupled surface polaritons, an increased sensitivity may be achieved as compared to standard SPR-based sensors. Furthermore, by using a material with a complex permittivity with an imaginary part being greater than or similar to the real part, the wavelength spectrum at which SPR-type biosensors operate can be expanded, since materials fulfilling this criteria can be found at most wavelengths. Metal-based SP-type biosensors are limited to wavelengths where metals behave as good conductors. While of course, optical wavelengths used with metal-based SP-sensors are important due to the availability of inexpensive LED lasers, not all bio-molecules are most preferably measured at optical wavelengths. Some bio-molecules may possess a higher change in refractive index at other wavelengths regions. By providing a sensor in accordance with the present invention, a sensor may be provided with is suited for the desired bio-molecule, and not the other way around.

By specifying that the sensor layer is of a material having a complex permittivity with an imaginary part being greater than or similar to the real part it is generally specified, in terms of permittivity, that the sensor layer is of a material generally referred to as an absorbing material. For this reason reference is also made to an absorbing material in the present disclosure.

The imaginary part of the permittivity may be similar to the real part. In general the imaginary part of the permittivity should be equal to or greater than the real part, however materials may exist which generally behave as an absorbing material but where the imaginary part of the permittivity is slightly smaller than the real part. For this reason, similar to should be understood as the imaginary part may be equal to or a few percent smaller than the real part of the permittivity, such as 3% smaller, 2% smaller or even less than 1% smaller.

The imaginary part of the permittivity may be greater than the real part of the permittivity. In embodiments, it may be 1 times greater, 2 timers, 5 times greater, 10 times greater or 100 times or even more times greater. The ratio between the imaginary part and the real part may depend upon the specific intended use and materials choice. For some embodiments, a given upper limit may be preferred since the larger the ratio, the more delocalized is the evanescent field, and with too large a ration one may loose the sensitivity towards smaller molecules.

In an embodiment, the real part of the permittivity of the sensor layer is positive. By specifying that the real part is positive, it is specified in terms of permittivity, that the sensor layer is a dielectric layer.

It is an advantage of embodiments of the present invention that absorbing materials exist at a wide range of wavelengths. Depending on the specific choice of material, the sensor layer may support excitation of surface polaritons at any wavelength ranging from the deep UV range to the far infrared range. In specific embodiments the wavelength range may be adapted to a specific light source, such as a lights source capable of providing radiation in a given sub-range. In a specific embodiment, the wavelength range may be in the UV wavelength range, such as in the range between 200 nm and 400 nm. No metallic sensor materials can be found which support surface polariton excitation in the UV range.

It is an advantage of embodiments of the present invention, that there exist a large number of materials having a complex permittivity with an imaginary part being greater than or equal to the real part. Of specific materials, the sensor material may be selected from the group consisting of, but not limited to: silicon, including crystalline and amorphous silicon, germanium, a phase change material, such as chalcogenide glass, as used in rewriteable optical recording and absorbing polymers. All these materials are well known in terms of industrial scale processing, facilitating easy fabrication of an assembly in accordance with embodiments of the present invention. Of specific interest is silicon due to the technological advantages over other materials. For example, down-scaling of surface polariton circuits using standard silicon compatible technology. Moreover, the surface chemistry of silicon is very well studied.

It is an advantage of embodiments of the present invention, that semi-conductor materials, such as silicon and other materials can be used, since the sensor material may be doped by one or more carrier species or provided with a specific impurity level. This opens up the possibility of electrical control or modification of the sensor so as to provide an active sensor having a possibly of tuning or switching the response. That is, to be able to electronically control whether or not the material of the sensor layer behaves as an absorbing material or as a non-absorbing material.

In an embodiment, the sensor material is of a thickness between 3 nm and 100 nm. The desired thickness may depend upon a number of factors, including but not limited to the specific material choice. It may be advantageous to use as thin a layer as possible for a given material, since in general as the layer becomes thinner, the width of the resonances decreases and thereby the resolution of the sensor increases. The thickness of the material may generally be selected in accordance with a general ability to excite a long-range surface exciton polaritons (LRSEP).

In embodiments the assembly further comprises a surface polariton coupler for coupling energy into a surface polariton mode of the sensor layer. The surface polariton coupler may in different embodiments be a structuring, such as a roughening, of the surface. The surface polariton coupler may be a dielectric grating structure positioned in the radiation path between an intended radiation source and the conductive layer. The surface polariton coupler may however typically be in the form of a prism or a hemispherical glass block positioned in contact with the substrate. Thus, various embodiments of surface polariton couplers are supported by the invention, ensuring a versatile assembly for coupling energy into a desired surface polariton mode.

In an advantageous embodiment, the top surface of the sensor layer is functionalized by chemical receptors. The top surface is the surface which is contacted to the target. The term functionalized should at least be construed as the top surface of the sensor layer comprises functional molecules. Functional molecules may act as capture probes capable of binding analyte or target molecules.

It may be important to ensure that the liquid analyte comprising the target and the carrier substrate are refractive index matched, in order to ensure that the sensor layer may support long range surface exciton polaritons. To this end refractive index matched may be that only a difference of few percents exists, such a difference of below 5%, below 3% or even below 1%.

In an embodiment, the sensor layer may comprise a plurality of areas so as to provide a micro-array suitable for use in a bio-assay. Each area of the plurality of areas may be provided with the same or different functionalities. By providing each area with same functionality a large number of different targets may efficiently be analyzed on the same assembly, whereas by providing each area with different functionalities, the same target may efficiently be analyzed with respect to large number of functional molecules. A micro-array suitable for screening applications may thereby be provided.

In a second aspect, the invention relates to an optical detection system for detecting a target, the optical detection system comprising:
 an assembly in accordance with the first aspect of the invention;
 a radiation source configured to cause excitation of a surface polariton mode in the sensor layer of the assembly; and
 a detector configured to detect resulting emission.

In a third aspect, the invention relates to a method for detecting the presence of a target on an assembly in accordance with the first aspect of the invention, the method comprises:
 exposing the sensor surface of the assembly to the target;
 exposing the sensor layer of the assembly to excitation radiation, the excitation radiation being capable of exciting a surface polariton mode in the sensor layer of the assembly; and
 detecting the resulting emission from the target with a radiation detector.

In connection with the second and third aspects of the invention, the radiation may be electromagnetic radiation in the optical range, the infrared (including far infrared) or ultraviolet range (including deep UV). The radiation may be polarized radiation, such as linearly polarized or circularly polarized radiation. One of the radiation source and the detector may be configured to emit/detect the emission from the substrate side of the assembly. A sensor may thereby be provided where one of or neither of the excitation and the emission radiation have to pass through the target sample. The radiation may be configured to excite a long-range surface exciton polariton (LRSEP) of the sensor material.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIG. 1 schematically illustrates an assembly in accordance with embodiments of the present invention.

DETAILED DESCRIPTION OF THE INVENTION

The present invention relates to the challenges of detecting low concentrations of a biological component, .i.e. the target, in a liquid analyte mixture. In a general embodiment, this may be achieved by selective capturing of the target with a binding composition, which is attached to a solid surface and detect associated spectral shift in the surface polariton resonances. The present invention provides a biosensor which is based on long-range surface polaritons in absorbing thin layers.

Figure 1:
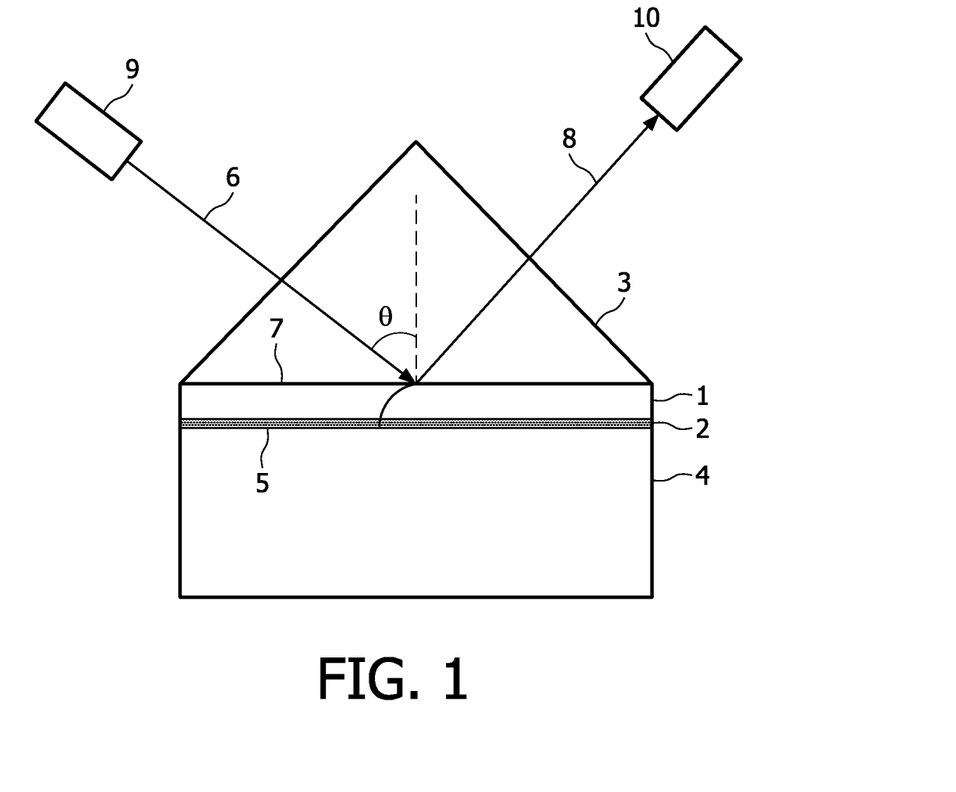

FIG. 1 schematically illustrates an assembly 1, 2 in accordance with embodiments of the present invention. The assembly comprises a substrate 1 and a sensor layer 2 positioned on the substrate. The assembly also comprises a surface polariton coupler 3 for coupling energy into a surface polariton of the sensor layer. Here the surface polariton coupler is in the form of a prism.

In a general detection situation, the assembly is exposed to a target, typically in the form of a flow of liquid analyte mixture or biological sample. Here the analyte mixture is schematically illustrated by a dielectric medium 4. In general, however, the target is typically a biological, chemical or biochemical component or molecule. In embodiments, capture probes or chemical receptors are bound to a surface 5 of the sensor layer (the top surface). The capture probes can bind target molecules in a biological liquid. The capture probe and target molecule form a complex that is bound to the top surface of the conducting layer. The associated resonance of the surface polariton of the capture probes is different from the associated resonance of the surface polariton of the capture probe-target molecule complex, and the shift in resonance can be measured. Alternatively worded, a refractive index shift is obtained in the dielectric material 4, giving rise to a shift in the resonance position.

The material of the substrate is in embodiments a dielectric substrate having a refractive indexed which is matched to the liquid analyte mixture exemplified with the dielectric medium indicated by reference numeral 4, or vice versa. A substrate material having a refractive index of 1.33 which is equal to water may be selected. As an example of a substrate material, a $SiO_x$-material may be used.

Radiation 6 as emitted from a radiation source 9 is incident onto the interface between two dielectrics, here the interface 7 between the prism 3 and the substrate 1, at an angle θ larger than the total internal reflection angle. The transmitted evanescent field may couple to a surface guided mode into the sensor layer 2. When coupling takes place, the specular reflection is reduced. For an absorbing sensor layer, a long range surface exciton polariton (LRSEP) may be excited in the sensor layer.

The resulting out-coupled radiation 8 is detected by an appropriate detector or sensor, such as by a CCD-based sensor for monochromatic radiation at a wavelength of $\lambda_0$ or a spectrometer for white light or broad band radiation.

In general different types of long range guided modes can be supported by thin films symmetrically surrounded by a non-absorbing dielectric. The specific mode can be classified according to the values of the complex permittivity of the thin layer. Long-range surface plasmon polaritons exist when the permittivity has a negative real value and a small imaginary value $|\epsilon_{real}|>>\epsilon_{imaginary}$ and $|\epsilon_{real}|>\epsilon_{dielectric}$. $TM_0$ modes are supported by films of positive permittivity in which $\epsilon_{real}>>\epsilon_{imaginary}$ and $\epsilon_{real}>\epsilon_{dielectric}$. Long range surface exciton polariton exists when $\epsilon_{imaginary}$ are greater than or similar to $\epsilon_{real}$ (independent of the sign of $\epsilon_{real}$). There is an important difference between a generic $TM_0$ guided mode and LRSP modes. A $TM_0$ mode is a bulk mode resulting from the coupling of the fields at the two surfaces of the thin film by means of total internal reflection; it is not a mode due to the interaction between two surface modes at opposite interfaces.

Figure 2A:
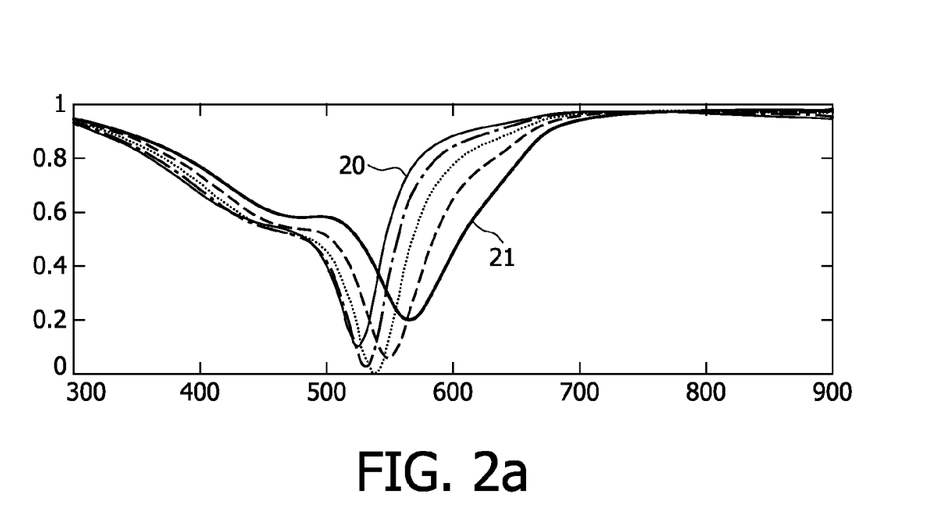
FIG. 2 illustrates calculations of the reflectivity as a function of the wavelength for a thin film of gold as the sensor layer and a thin film of amorphous silicon as the sensor layer.
Figure 2B:
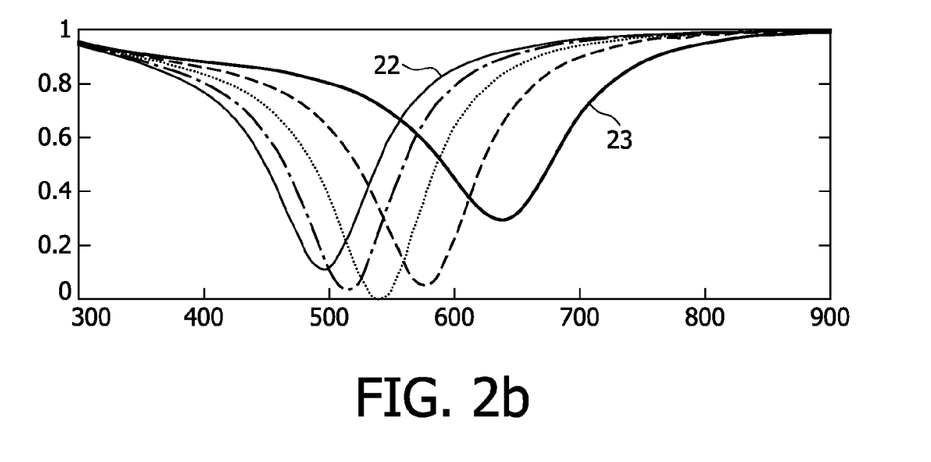

FIG. 2 illustrates calculations of the reflectivity (horizontal axis) as a function of the wavelength (vertical axis) in an assembly as illustrated in FIG. 1 for a 20 nm thin film of gold as the sensor layer and a 480 nm thin substrate (FIG. 2A) and a 20 nm thin film of amorphous silicon (a-Si) and a 400 nm thin substrate (FIG. 2B). The unit of the wavelength is nanometer (nm). Silicon has a complex permittivity in the wavelength range and silicon is an absorbing dielectric at the wavelength used in the calculations.

In FIG. 2A the refractive index of the dielectrics layer 4 is varied around 1.33 at an angle of incidence of 53.1 degrees. The Figure shows the result of n=1.33 as indicated by reference numeral 20, to n=1.35 at reference numeral 21, with increments of 0.05 for the curves in-between. In FIG. 2B the refractive index of the dielectrics layer 4 also varied around 1.33, but at an angle of incidence of 52.7 degrees. The Figure shows the result of n=1.33 as indicated by reference numeral 22, to n=1.35 at reference numeral 23, with increments of 0.05 for the curves in-between. As can be seen a shift of the resonance occurs for both a gold sensor layer and a silicon sensor layer.

Figure 3:
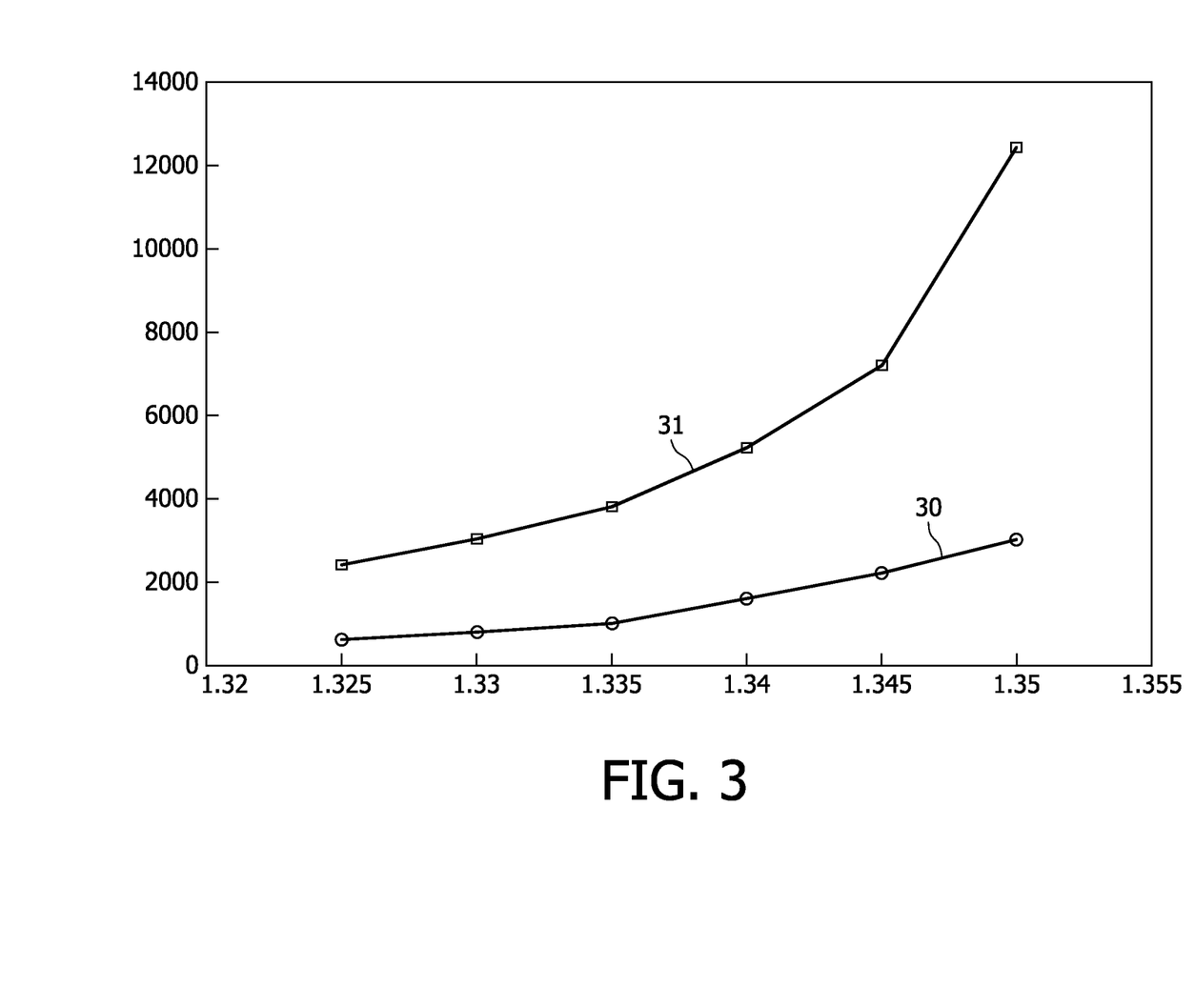
FIG. 3 shows a graph of the sensitivity of the assembly of FIG. 1.

FIG. 3 shows a graph of the sensitivity of the assembly of FIG. 1. The graph shows the sensitivity in terms of the ratio $\Delta\lambda/\Delta n$ along the vertical axis, as a function of the refractive index n along the horizontal axis for the two configurations of FIGS. 2A and 2B, that is for a 20 nm gold film, a 400 nm substrate at an angle of incidence of 53.1 degrees (reference numeral 30) and for a 20 nm amorphous silicon film, a 480 nm substrate at an angle of incidence of 52.7 degrees (reference numeral 31). The sensitivity is defined as the shift of the resonance as the refractive index of the medium in contact with the sensor layer is changed (the medium with reference numeral 4 in FIG. 1. As can be seen the sensitivity of a layer of amorphous silicon is greater than the sensitivity of a gold layer.

Figure 4:
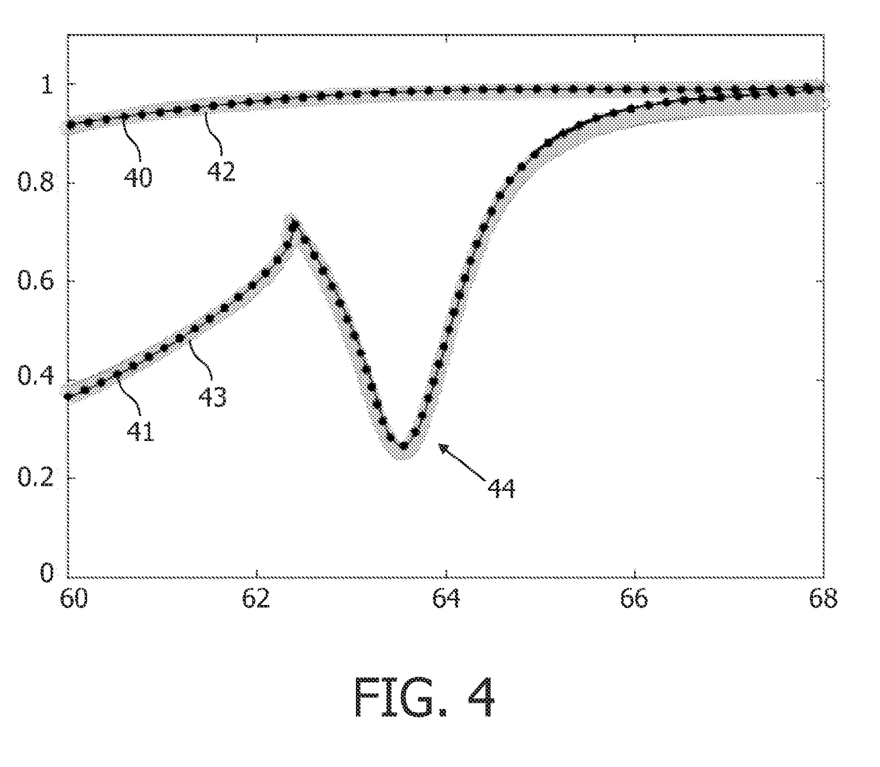
FIG. 4 shows calculations and experimental results for a system of amorphous silicon sputtered onto a quartz substrate and covered with 350 nm of $SiO_2$.

Application of an absorbing sensor layer renders it possible to provide an assembly suitable for radiation at wavelengths that are not applicable with metallic sensor layers. FIG. 4 illustrates a calculation of the reflection of a thin amorphous silicon sensor layer in an attenuated total reflection measurement at a wavelength of 375 nm which is in the ultraviolet spectral region. No suitable metals are available at this wavelength.

FIG. 4 shows the reflectivity along the vertical axis as a function of the angle of incidence (degrees) along the horizontal axis. The Figure shows calculations and experimental results for a system where a 13 nm of amorphous silicon (a-Si) is sputtered onto a quartz substrate and covered with 350 nm of $SiO_2$. FIG. 4 shows the calculated results as dotted lines 40, 41 and the experimental results as broad grey lines 42, 43. The theoretical curves have been obtained by leaving the thickness of the $SiO_2$ and the a-Si layers as free parameters to fit to the measurements. The permittivities of the a-Si and the $SiO_2$ were determined from ellipsometry measurements and these values were kept fixed in the fits. The calculations and measurements have been performed for both for p- and s-polarized light. The result for s-polarized light is indicated with reference numerals 40, 42, whereas the results for p-polarized light is indicated with reference numeral 41, 43. The measurements and calculations of the p-polarized reflection 41, 43 have a sharp dip 44 at an angle of 63.6 degrees, larger than the angle of total internal reflection at 62 degrees. At the resonance angle, the momentum of the evanescent transmitted beam through the prism-$SiO_2$ interface matches the momentum of the LRSP and coupling is possible, giving rise to the reduction of the reflection. For a wavelength of 375 nm, the absorption in a-Si is very strong ($\in$=10.8+19.9i) and the minimum in the reflection can be attributed to coupling to LRSPs. No particular features are found in the s-polarization as for this polarization it is not possible to excite LRSPs. A good agreement between the experimental result and the calculated result is found.

In the present disclosure, such parameters as thickness, material choice and other structural parameters are disclosed in connection with description of different embodiment. It is to be understood a large number of variations within the scope of the invention is possible for the skilled person. Moreover, in a measurement, a number of parameters may need to be correlated. For example, an assembly with a specific configuration may be selected in accordance with a desired target to be detected and the excitation wavelength, or vice versa, in order to be able to excite the desired SP mode. Also a specific substrate material may be selected, etc.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. An assembly for detecting presence of a target, the assembly comprising:
    a carrier substrate; and
    a sensor layer positioned over the carrier substrate;
        wherein the sensor layer is a material having a complex permittivity with an imaginary part being greater than or equal to the real part.

2. The assembly according to claim 1, wherein the real part of the permittivity is positive.

3. The assembly according to claim 1, wherein the sensor layer is configured to support excitation of coupled surface polaritons in the UV-wavelength range.

4. The assembly according to claim 1, wherein the sensor material is a material selected from the group consisting of: Silicon (Si), Germanium (Ge), a phase change material, and absorbing polymers.

5. The assembly according to claim 1, wherein the sensor material is doped by one or more carrier species.

6. The assembly according to claim 1, wherein the sensor material has a thickness between 3 nm and 100 nm 7. The assembly according to claim 1, wherein the assembly further comprises a surface polariton coupler configured to couple energy into a coupled surface polariton mode of the sensor layer.

8. The assembly according to claim 1, wherein a top surface of the sensor layer is functionalized by chemical receptors.

9. The assembly according to claim 1, wherein a liquid analyte comprising the target and the carrier substrate are refractive index matched.

10. The assembly according to claim 1, wherein the sensor layer comprises a plurality of functional areas so as to provide micro-array suitable for use in a bio-assay.

11. An optical detection system for detecting a target, the optical detection system comprising:
    an assembly comprising:
        a carrier substrate; and
        a sensor layer positioned over the carrier substrate;
        wherein the sensor layer is a material having a complex permittivity with an imaginary part being greater than or equal to the real part;
    a radiation source configured to cause excitation of a surface polariton mode in the sensor layer of the assembly via an emitted excitation radiation; and
    a detector configured to detect a corresponding resulting emission caused by the excitation radiation.

12. A method for detecting the presence of a target on an assembly, the method comprising:
    exposing a sensor surface of an assembly to the target, the assembly comprising:
        a carrier substrate; and
        a sensor layer positioned over the carrier substrate;
        wherein the sensor layer is a material having a complex permittivity with an imaginary part being greater than or equal to the real part;
    exposing the sensor layer of the assembly to excitation radiation, the excitation radiation being capable of exciting a surface polariton mode in the sensor layer of the assembly; and
    detecting a corresponding resulting emission from the target caused by the excitation radiation with a radiation detector.

13. The optical detection system according to claim 11, wherein the real part of the permittivity is positive.

14. The optical detection system according to claim 11, wherein the sensor material is a material selected from the group consisting of: Silicon (Si), Germanium (Ge), a phase change material, and absorbing polymers.

15. The optical detection system according to claim 11, wherein the sensor material has a thickness between 3 nm and 100 nm 16. The optical detection system according to claim 11, wherein a top surface of the sensor layer is functionalized by chemical receptors.

17. The method of claim 12, wherein the real part of the permittivity is positive.

18. The method of claim 12, wherein the sensor material is a material selected from the group consisting of: Silicon (Si), Germanium (Ge), a phase change material, and absorbing polymers.

19. The method of claim 12, wherein the sensor material has a thickness between 3 nm and 100 nm 20. The method of claim 12, wherein a top surface of the sensor layer is functionalized by chemical receptors.

* * * * *

UNITED STATES PATENT AND TRADEMARK OFFICE
CERTIFICATE OF CORRECTION

PATENT NO. : 8,629,983 B2  
APPLICATION NO. : 13/120737  
DATED : January 14, 2014  
INVENTOR(S) : Forcales et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Twenty-second Day of September, 2015

Michelle K. Lee
*Director of the United States Patent and Trademark Office*